United States Patent [19]
Berndt

[11] Patent Number: 5,397,709
[45] Date of Patent: Mar. 14, 1995

[54] SYSTEM FOR DETECTING BACTERIAL GROWTH IN A PLURALITY OF CULTURE VIALS

[75] Inventor: Klaus W. Berndt, Stewartstown, Pa.

[73] Assignee: Becton Dickinson and Company, Franklin Lakes, N.J.

[21] Appl. No.: 113,444

[22] Filed: Aug. 27, 1993

[51] Int. Cl.$^6$ ............................ C12Q 1/04; C12M 1/34
[52] U.S. Cl. ...................................... 436/34; 356/442; 422/82.05; 422/82.09; 435/291; 435/808
[58] Field of Search ................... 435/4, 29, 34, 291, 435/808; 356/432, 434, 436, 440, 441, 442, 244, 246; 422/62, 63, 67, 68.1, 82.05, 82.08, 82.09; 436/50, 164, 165, 171

[56] References Cited

U.S. PATENT DOCUMENTS

| | | | |
|---|---|---|---|
| 3,773,426 | 11/1973 | Mudd | 356/434 |
| 4,055,470 | 10/1976 | Sheaff et al. | 435/808 X |
| 4,115,010 | 9/1978 | McAleer et al. | 356/440 |
| 4,116,775 | 9/1978 | Charles et al. | 435/808 X |
| 4,201,478 | 5/1980 | Gerlier et al. | 356/440 |
| 4,349,510 | 9/1982 | Kolehmainen et al. | 435/808 X |
| 4,397,560 | 8/1983 | Andresen | 356/440 |
| 4,498,780 | 2/1985 | Banno et al. | 356/244 X |
| 4,678,894 | 7/1987 | Shafer | 435/808 X |
| 4,762,420 | 8/1988 | Bowley | 356/440 X |
| 4,931,402 | 6/1990 | Abplanalp | 435/291 |
| 4,945,060 | 7/1990 | Turner et al. | 435/287 X |
| 5,082,628 | 1/1992 | Andreotti et al. | 435/808 X |
| 5,096,835 | 3/1992 | Yokomori et al. | 356/440 X |
| 5,158,748 | 10/1992 | Obi et al. | 422/63 X |

Primary Examiner—Jill A. Johnston
Attorney, Agent, or Firm—Alan W. Fiedler

[57] ABSTRACT

A system for detecting the presence of bacterial growth in a plurality of sample vials incorporates a single test station moveable along each of the plurality of sample vials. In one embodiment, the sensor station is movably mounted on a rod, and that rod is movably mounted on a pair of spaced rods. The rod which carries the test station may move along the spaced rods to change the location of the test station in a first dimension and the test station is moveable along its rod to change location in a second dimension. In this way, the test station may be moved through two dimensions to move serially to the location of each of the plurality of sample vials. In another aspect of this invention, a bar code is associated with each of the sample vials, and the test station makes a reading of that bar code concurrent with a determination being made as to whether there is any bacterial growth in the sample vial. In this way, it is ensured that the results of the evaluation of whether bacterial growth is ongoing will be associated with the proper sample vial. In a third aspect of this invention, the sample vial incorporates a plurality of distinct types of bacterial sensors. Thus, the advantages of each of several types of bacterial sensors may be incorporated into a single sample vial.

13 Claims, 13 Drawing Sheets

SYSTEM FOR DETECTING BACTERIAL GROWTH IN A PLURALITY OF CULTURE VIALS

BACKGROUND OF THE INVENTION

This application in general relates to an improved system for monitoring a plurality of sample vials, and making a determination of whether the sample vials are experiencing bacterial growth.

Sample vials are prepared by injecting a body fluid sample into a culture medium in a sample vial. The sample vial is then incubated, and tested for bacterial growth. Systems for detecting bacterial growth in sample vials are known, wherein a large number of sample vials are repeatedly and periodically tested for the presence of bacterial growth. Several types of sensors are known which have changing responses to a light input based on conditions within the sample vial. By monitoring the sensor response one can determine whether there is bacterial growth.

Generally, in known sensors light is directed into the sample vial or sensor. Light reemerging from the sample vial, or from the sensor, is monitored to determine whether bacterial growth is occurring in the sample vial. Such sensors and associated methods of determination are known in the art, and the types of changes which indicate bacterial growth are known.

Known test systems typically hold a large number of such sample vials. In one example, they hold 240 sample vials. With the known systems an individual light source, an individual photodetector and the required wiring are associated with each sample vial. Thus, such systems are complicated and expensive. Due to the large number of light sources and detectors which are required, such systems have sometimes utilized less expensive light sources or detectors than those which may be most desirable. Also, since several hundred light sources and photodetectors are utilized within each system, station to station variations are inevitable. That is, a light source associated with a first station may emit light at a different intensity than the other stations. Variation could also occur between the photodetectors associated with the hundreds of stations. This could result in potential variations in readings between vials within the system. Such variations are undesirable.

Another problem with the prior art systems is that the only identification of a vial located at a particular station within the system is by a manual bar code reading before the vial is placed into the station. Thus, if an operator misplaces the vial within the station, there may be misidentification of the location of the vial within the station.

Finally, as discussed above, there are several types of sensors which may be utilized to determine the presence of bacterial growth. Each type of sensor has beneficial characteristics, and other characteristics that are undesirable. Further, certain types of bacteria are better detected by certain types of sensors. Thus, no one single type of sensor provides all desirable characteristics. Even so, the prior art has typically utilized vials with only a single type sensor incorporated into the vial.

SUMMARY OF THE INVENTION

In a disclosed embodiment of this invention, a single test station includes a light source and a light detector, and periodically and serially tests each of the sample vials. In a preferred embodiment of this invention, the sample vials are arranged in a two dimensional array. The test station is mounted on a frame which moves along both of the dimensions to test each vial.

Since a single test station tests each of the hundreds of vials, more expensive light sources and detectors may be incorporated while still reducing the cost of the overall system. More importantly, since only a single source and detector are utilized, station to station variations such as experienced with the prior art systems are eliminated.

Several embodiments of this basic concept are disclosed in this application. The several embodiments incorporate the necessary apparatus for many of the several types of sensors which may be utilized to test sample vials.

In one preferred embodiment of this invention, the test station carries only an optical fiber. The optical fiber is operably connected to a source of light, and to a photodetector. Thus, the moving test station frame need not carry any heavy equipment, or any cables to supply power to equipment mounted on the frame. Rather, the frame need only move the optical fiber.

In a second aspect of this invention, a bar code is formed on the sample vial, and the test station includes structure for reading the bar code from the sample vial. The bar code information is then positively associated with the test results from the vial. In this way, the results of the test are tied to the particular sample vial, and a misidentification of test results will not occur.

In a preferred embodiment of this invention, the bar code is printed on a label associated with the sample vial, and a reference indicia is placed adjacent to the bar code. The bar code and reference indicia are preferably printed on a single label. Thus the reference indicia and bar code are always at known locations relative to each other. The test station may read the position of the reference indicia to ensure that the sensor station is properly positioned relative to the bar code prior to reading the bar code. Further, the reference indicia insures the test station is properly positioned relative to the sample vial. In this way, the test station properly reads the bar code, and eliminates misidentification due to mispositioning between the test station and the bar code.

In a most preferred embodiment of this invention, the bar code is printed in a circular pattern, and the reference indicia is a circle concentric to the bar code. A circular bar code pattern provides the greatest length for bar code information per unit space on the vial. Further, the circular bar code and reference indicia do not require any particular orientation of the sample vial about an axis of the sample vial relative to the test station.

In a third aspect of this invention, a sensor patch is placed on the bottom of the sample vial. The sensor patch includes a plurality of distinct types of sensors. As an example, sensors which respond to carbon dioxide concentration, pH level, oxygen level or other types of changes in the sample vial may all be associated with each vial. In this way, a test station can test each of these various types of sensors, and make a more informed determination of whether the particular sample vial is experiencing bacterial growth.

These and other features of the present invention can be best understood from the following specification and drawings, of which the following is a brief description.

DETAILED DESCRIPTION OF THE PREFERRED EMBODIMENTS

Figure 1A:
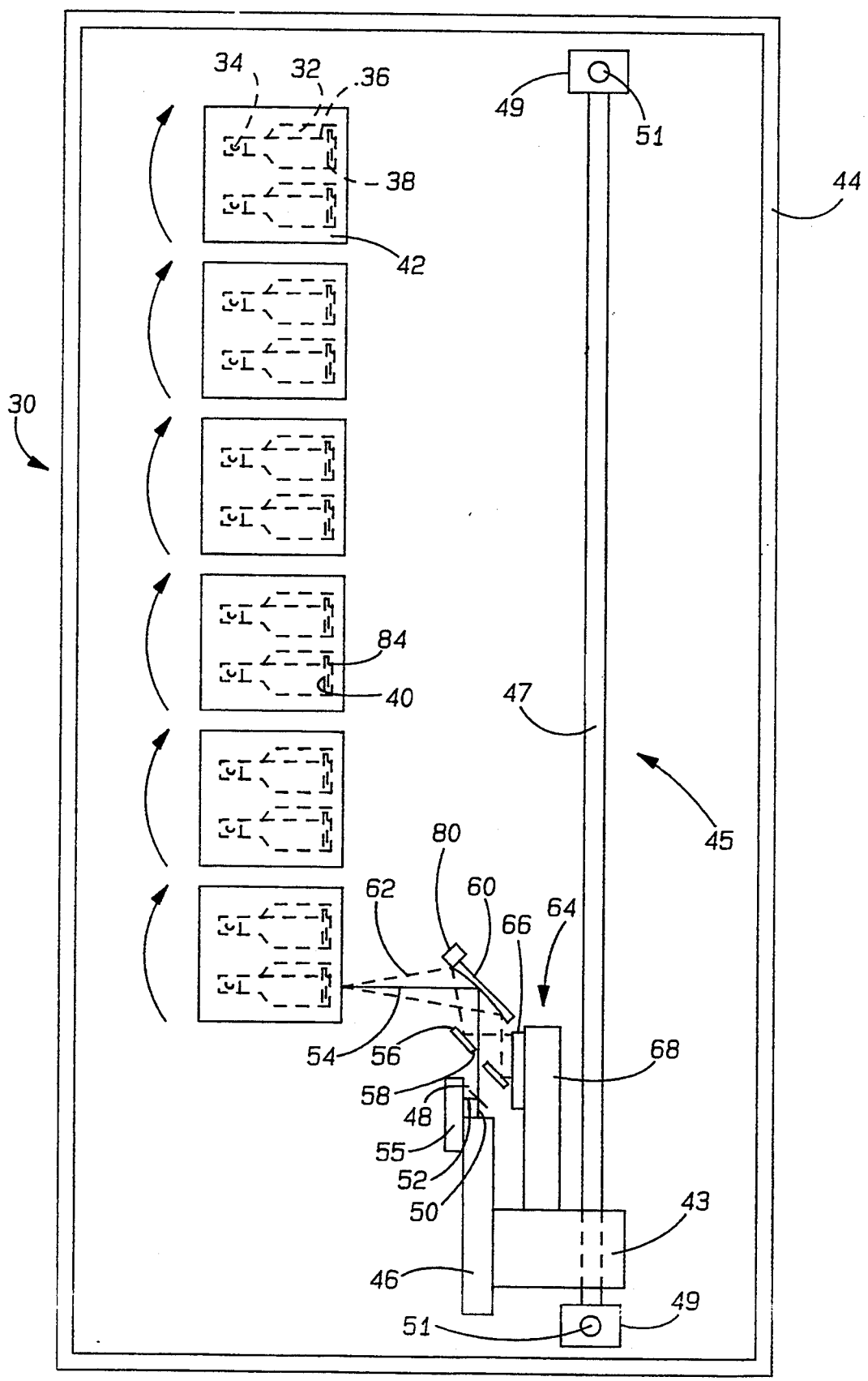
FIG. 1A shows a first embodiment of a system according to the present invention.

A first system 30 for intensity-based detection of microorganisms is shown in FIG. 1A. System 30 holds a plurality of vials 32, each sealed with a septum 34 and containing a medium/bodily fluid mixture 36. Typically, the body fluid is blood and the medium is prepared by known techniques. Each vial 32 contains an intensity-based chemical sensor 38 disposed on an inner bottom surface 40. While an intensity sensor is used with this embodiment, other sensors which generate a selective emission or change their reflectivity, opacity, or color in the presence of biological activity are known and may also be used. In other systems, the sample may be scanned without the use of a separate sensor associated with the vial, e.g., scattered photon migration ("SPM"), as discussed further below.

Two rows of vials 32 are arranged on each of several tipping racks. Tipping racks 42 are agitated to promote the growth of microorganisms within vials 32. Tipping racks 42 may be biased or held in a known hold position, such as that shown in FIG. 1, while a determination of biological activity may be made. In some applications it is desirable to hold the vials at an angle relative to the vertical to maximize the level of fluid. Any structure for moving the tipping rack, or holding it at the known position may be used. A plurality of tipping racks 42 are used since a tipping rack for as many as 240 vials would have considerable mass. Racks 42 contain only vials 32 and no electronic components and, consequently, no electrical wires. Vials 32 and tipping racks 42 are arranged inside a known type incubator 44 used to promote microorganism growth.

A single test station or carriage 43 is moved to test all of the vials. Light output is generated from a single high energy light source, such as laser 46, and is serially directed at sensors 38 on a large number of vials 32. Laser 46 and a detector module 64 are mounted on test station 43, which is movable as part of an XY translation stage 45. XY translation stage 45 allows for movement of test station 43 along a rod 47 that is fixed to two guide blocks 49. The blocks 49 move along perpendicularly arranged rods 51. If tipping racks 42, containing a total of 240 vials (12 rows and 20 columns) are used, a single XY translation stage 45 must be able to address a maximum of 20 vials in one direction. As an alternative, two (or more) test stations can be used with each testing plural vials.

Figure 1B:
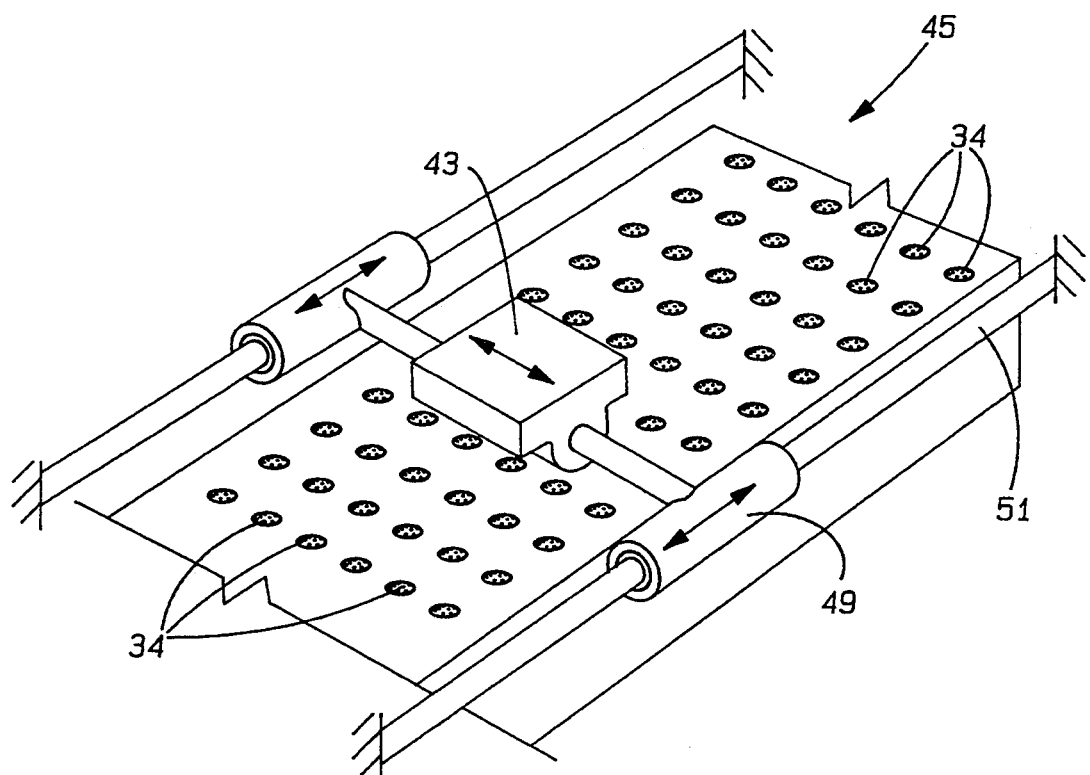
FIG. 1B is a partial end view, shown somewhat schematically, of a system according to the present invention.

In operation, a system controller described below, directs test station 43 from a home position to a first vial station. Each of the vials 32 are then serially tested. As shown in FIG. 1B, the XY translation stage 45 moves test station 43, which carries laser 46. A plurality of sample vials 32 are arranged in a two dimensional array. Rods 51 are positioned at the top and bottom of the vial array, and guide blocks 49 carry rod 47 along rods 51. In one embodiment, rods 51 could include a linear motor for driving guide blocks 49. Such linear motors are known, and may operate by passing current to move guide blocks 49 axially along bars 51. Similarly, test station 43 may move along bar 47 by use of a linear motor. In such a motor, test station 43 and guide blocks 49 would include magnets. By moving guide blocks 49 along rods 51, the location of test station 43 can be varied to the right and left as shown in FIG. 1B, and the up and down position of test station 43 as shown in FIG. 1B can also be varied by moving test station 43 along rod 47.

As stated above, rods 47 and 51 may incorporate linear motors which drive the guide blocks 49, and test station 43 and guide blocks 49 could incorporate magnets to be driven along the rods 47 and 51. Alternatively, any other known means of guiding the test station 43 through two dimensional movement may be utilized. Known x-y translators are used for navigation, plotting and printing. It is not the structure of the translator which is inventive, but rather the use of an x-y translator in this environment.

As shown in FIG. 1A, a beam splitter 48 is mounted on test station 43 and splits an output beam 50 from laser 46 into components 52 and 54. Reference beam component 52 is directed toward a reference photodetector 55. Reference photodetector 55 measures the intensity of reference beam component 52 and generates a reference photocurrent value corresponding to the measured intensity. Output beam component 54 passes through mirror 56 having central aperture 58, and is deflected off of a curved mirror 60 to contact and excite a sensor 38 of a selected vial 32. When excited by output beam component 54, sensor 38 generates an emission which varies with the presence of biological activity. In the illustrated embodiment, a fluorescence emission generated by the sensor increases in proportion to increased biological activity. Fluorescence intensity chemical sensors 38 are known which react to pH, oxygen concentration, carbon dioxide concentration, or in response to other biological activities.

An emission 62 from a particular sensor 38 is collected by curved mirror 60, planar mirror 56 and directed toward an optical sensing detector module 64 where the emission is monitored. Detector module 64 includes a spectral emission filter 66, and a high-sensitivity photodetector 68. Filter 66 is used to block unwanted short-wavelength or excitation radiation that can affect readings. Photodetector 68 measures the intensity of emission 62 and generates a sensor photocurrent value representative of the measured intensity.

In one preferred embodiment, laser 46 is a green helium neon (HeNe) laser having a wavelength in the range of about 543.5 nm, with approximately 1.5 mW of output power. The diameter of output beam 50 should be no greater than about 2 mm. The short-wavelength light and output power reacts well with a fluorescence sensor 38 in the presence of biological activity.

With this embodiment, and all other embodiments disclosed in this invention, the thrust of the invention is to the moving test station and associated structure, to bar code reading, and to a plural sensor embodiment as will be disclosed below. The parameters used to evaluate the readings made on the particular sensors are as known in the art. The present invention does not disclose any new testing logic. Rather, the detected emission, etc. are evaluated as known in the art to make a determination of whether a particular vial is experiencing bacterial growth.

Figure 2:
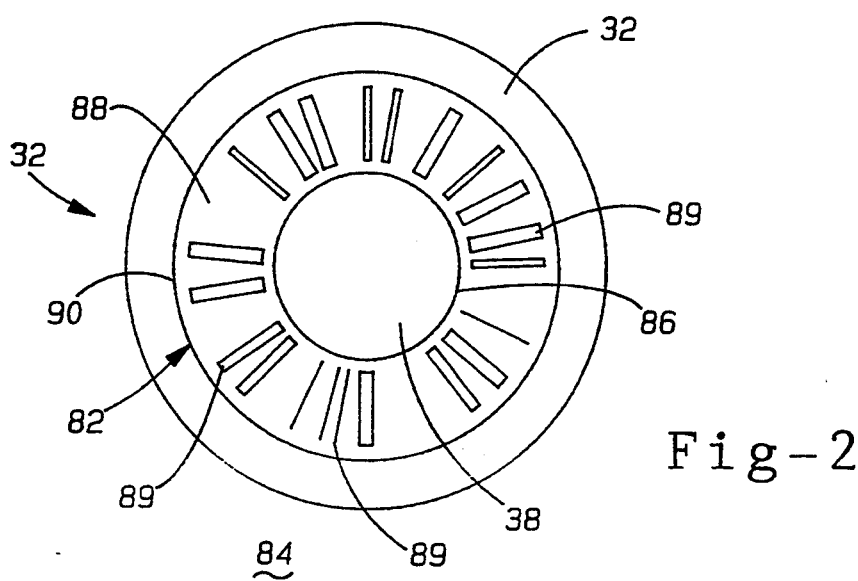
FIG. 2 shows a vial bottom with a central bacterial sensor and a bar code pattern.

The test station 43 carried on XY translation stage 45 also includes a monitor photodiode 80 for measuring light backscattered from a bar code label 82 shown in FIG. 2, preferably placed on a bottom outer surface 84 of vial 32. In the illustrated embodiment, bar code 82 includes a central opening 86 so that sensor 38 is exposed. In an alternative embodiment, bar code 82 may be printed on a label placed on bottom inner surface 40 which also includes sensor 38. A circular bar code pattern 88 comprises a plurality of marks 89 extending radially outwardly from central opening 86. The marks 89 carry information with regard to the vial, the sample, or the patient associated with the sample. Bar code pattern 88 includes a reference indicia, here an outer concentric circle 90. If used with a standard blood culture vial, bar code pattern 88 can have a diameter of approximately 25 mm. With such a diameter, the bar code information characterizing the vial can be distributed over a circle circumference length of 78.5 min. The effective length of a circular pattern is at a maximum compared to other patterns for any given vial diameter.

Figure 3:
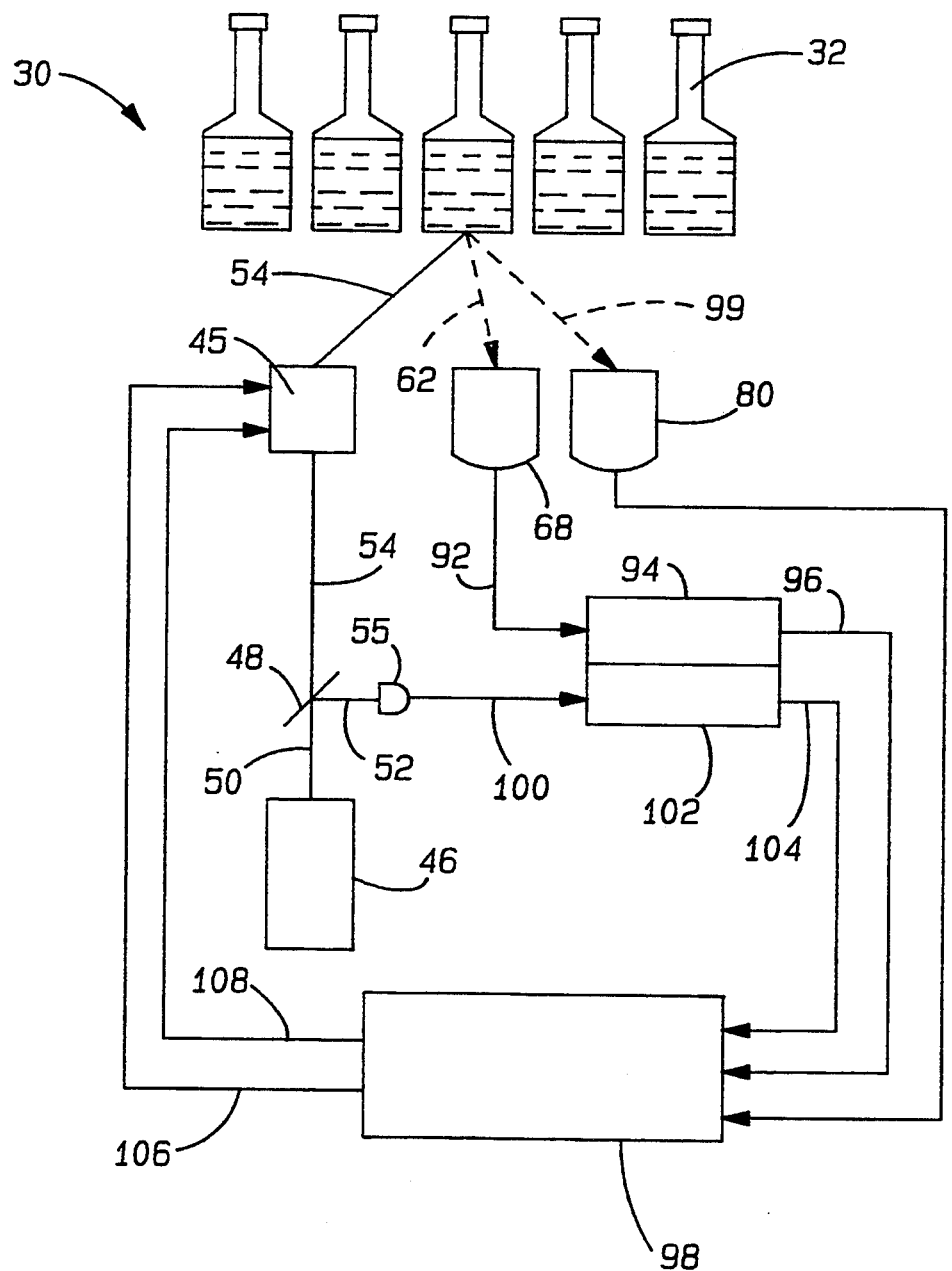
FIG. 3 is a schematic of a control system associated with the system of FIG. 1.

To read out the bar code information 88, small sinusoidal deflection signals are sent to XY translation stage 45 via X and Y output channels 106 and 108, as shown in FIG. 3. The two signals have equal amplitude, but show a phase difference of 90 degrees. This results in a movement of output beam component 54 along the circumference of a circle. The amplitude of laser 46 is adjusted and output beam component 54 scans bar code pattern 88 including concentric circle 90. This light is backscattered to be read by photodiode 80. If XY translation stage 43 is initially incorrectly positioned with respect to a vial 32, concentric circle 90 is used as a position encoder to more accurately position XY translation stage 45 with respect to a vial 32 before reading the bar code. The test station 43 moves until concentric circle 90 is read as being at an expected position relative to test station 43. The concentric circle 90 and bar code pattern 88 are printed onto a label at known relative positions.

In the embodiment of FIG. 1A, output beam component 54 is focussed onto vial bottom surface 84 using mirror 60. As mentioned above, the available geometrical length of the bar code pattern 88 is approximately 78.5 mm. Green HeNe lasers such as preferred for use in the FIG. 1 embodiment typically have beam diameters of 0.5 min. With such dimensions, no extreme focussing is required to read out the bar code information. However, when necessary, stronger focussing is accomplished very easily by a simple lens attached to laser 46.

Under some circumstances, a larger diameter for output beam component 54 may be desired. A small beam could result in sensor bleaching, since only a very small surface area of the sensor is exposed to the test light. To avoid such a result, output beam component 54 can be moved about a small circle. In other words, small sinusoidal deflection signals may be sent to XY translation stage 45 via the X and Y channels 106 and 108 continuously. To move from the above described circular movements for reading the bar code, and then to switch from bar code reading to sensor reading, only the amplitude of the sinusoidal signals would have to be changed.

Photodiode 80 is not necessary if bar code pattern 88 is printed using a dye which fluoresces within the same wavelength range as the emission from sensor 38. In this way, the same detector module 64, including photodetector 68, can be used for microorganism detection and for bar code reading.

A major advantage of system 30 is that both laser 46 and detector module 64 may be moved closely to individual vials 32. Therefore, an extremely high spatial resolution for the bar code reading and improved light detection sensitivity can be realized. Further, greater accuracy is achieved by using a single test station for many vials in place of individual devices for each vial. More expensive and precise instrumentation can be used at a reasonable cost. Further, the need for instrument calibration is greatly reduced, if not eliminated by the present invention.

As known, vials 32 are continuously scanned until either there is a presence of biological activity, or a predetermined period of time, typically five days, has passed. Generally, the presence of biological activity in a vial is indicated by a pronounced change in the measured sensor emission 62.

As shown schematically in FIG. 3, laser 46 generates an output beam 50. Beam splitter 48 splits output beam 50 into reference beam component 52 and output beam component 54. With XY translation stage 45, shown in FIG. 1, correctly positioned, output beam component 54 is directed to a preselected sensor 38 associated with a vial 32. The sensor then generates an emission 62. Photodetector 68 monitors emission 62 and generates a sensor photocurrent 92. Photocurrent 92 is routed to a detector DC meter 94. An output 96 from DC meter 94 is fed to a controller 98, such as a computer.

Reference beam component 52 is directed to reference photodetector 55, which monitors reference beam component 52 and generates a reference photocurrent 100. Photocurrent 100 is routed to a reference DC meter 102. An output 104 from meter 102 is also fed into controller 98. If the reference beam component 52 varies from an expected value, then the intensity of output beam 50 is also not as expected, or desired. The intensity of output beam 50 is adjusted as necessary.

Controller 98 stores and analyzes outputs such as 96 and 104 to make a determination concerning microorganism growth. As is known, controller 98 compares incoming data to earlier collected data. In addition to collecting and analyzing information, controller 98 positions XY translation stage 45, with signals being sent through X output channel line 106 and Y output channel line 108. Known control logic is used for moving station 43 as desired. Thus, output beam component 54 is directed serially from vial to vial allowing a determination of microorganism growth to be made for each vial 32. Backscattered light 99 may be detected by photodetector 80, as discussed above, to accurately position XY translation stage 45 and read the bar code information.

Figure 4:
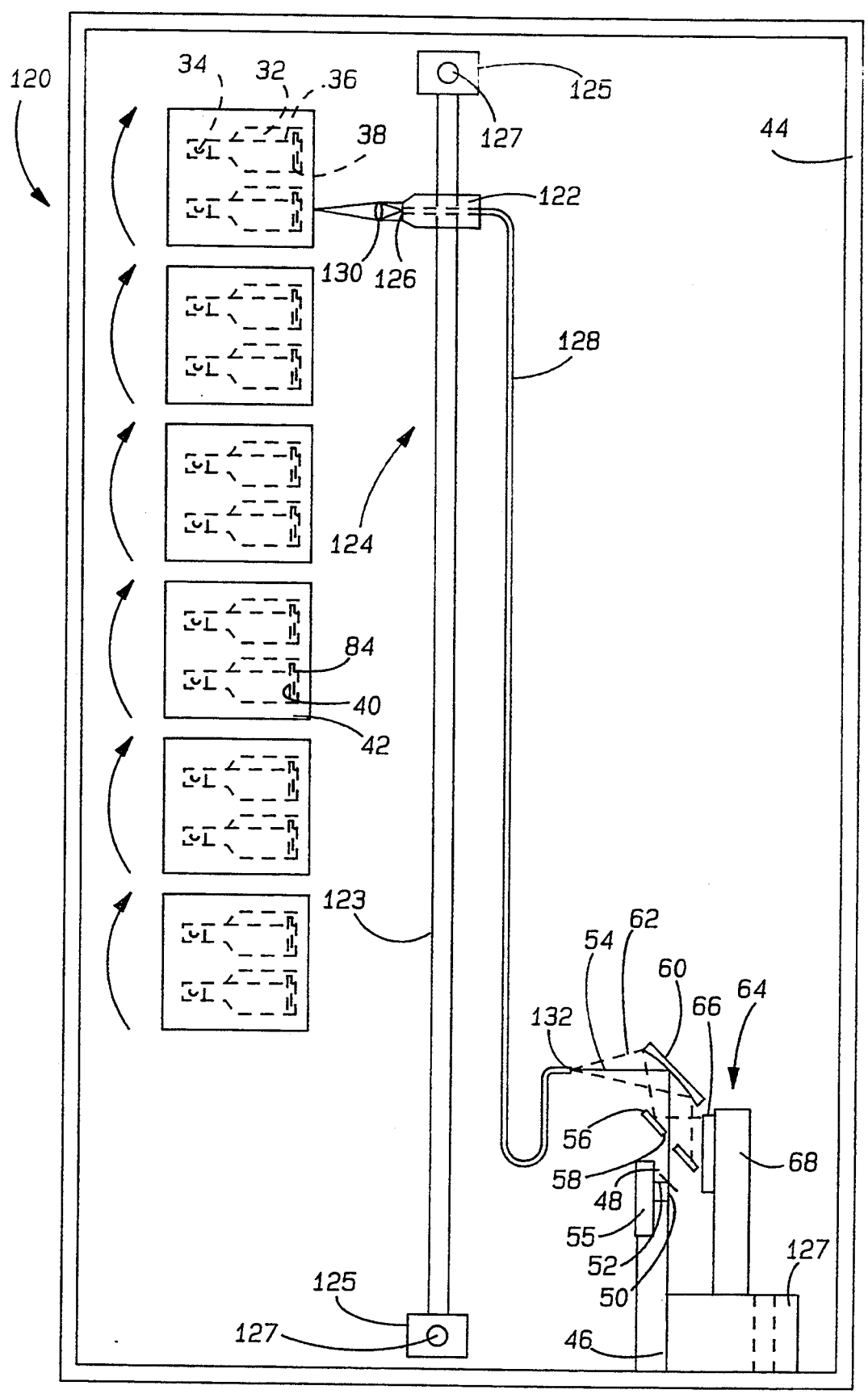
FIG. 4 shows a second embodiment of a system according to the present invention.

A typical green HeNe laser head of 0.2 mW output power only has a weight of 0.34 kg and a length of 25 cm. However, it still needs a high-voltage power cable. Similar considerations apply to high-sensitivity photodetectors such as photomultipliers. Thus, in the FIG. 1A embodiment cables must extend from the moving test station to a fixed power source and to the controller. These requirements are addressed by system 120 as illustrated in FIG. 4. A test station 122 is arranged on an XY translation stage 124. As in the embodiment of FIG. 1, XY translation stage 124 allows for movement of test station 122 along a rod 123 that is fixed to two guide blocks 125. In turn, the blocks 125 can move along perpendicularly arranged rods 127. Test station 122 holds an output end 126 of an optical fiber 128, and an imaging lens 130. In this embodiment, laser 46 and detector module 64 are mounted to a pedestal 127 in close proximity to one another at a fixed position within system 120. The input end 132 of fiber 128 is mounted so that it receives the full optical output of output beam component 54. Light travels along fiber 128 and reaches output end 126. Beam component 54 exiting fiber output end 126 is imaged onto bottom inner surface 40 of vial 32. An emission 62 reemerging from surface 40 is refocussed by lens 130 into output end 126, back along fiber 128 and out input end 132. The emission 62 that emerges from input end 132 is directed by mirrors 60 and 56 through filter 66 and to photodetector 68.

A major advantage of system 120 is that a minimum amount of mass has to be moved on test station 122 for scanning an array of vials 32. In addition, no electrical cables or wires are required on moving test station 122. Output end 126 may be located closely to the bottoms of vials 32. In so doing, an extremely high bar code resolution and good light detection sensitivity are achieved. Sensor and bar code reading may be performed by moving the test station 122 as described above with respect to the embodiment of FIG. 1A. As an alternative, a pair of fibers may be used, with one directing light at the sensor, and one receiving emissions from the sensor.

Figure 5:
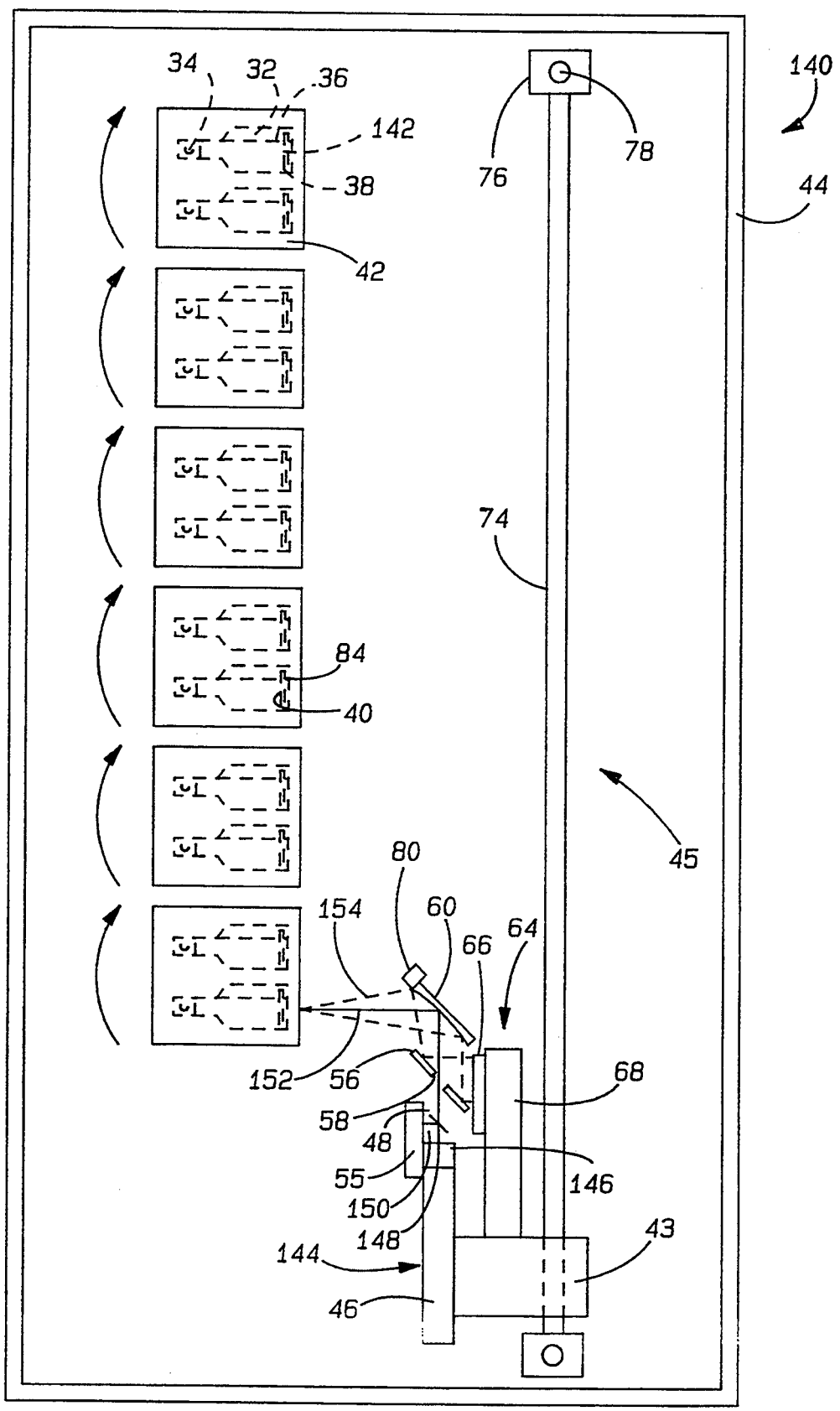
FIG. 5 shows a third embodiment of a system according to the present invention.

A third system 140 according to the present invention for use with time decay detection of bacteria, is shown in FIG. 5. System 140 is similar to system 30 illustrated in FIG. 1A. However, a different type of optical sensor, a fluorescence decay time sensor 142, is disposed on inner bottom surface 40 of each of vials 32. Fluorescence decay time sensors are known which change their decay time in response to changing pH, oxygen concentration, carbon dioxide concentration, or in response to other biological activities. Using this method, intensity measurements are replaced with time measurements, so intensity changes do not influence the results. For sensors 142 to work properly, a modulated light source 144 includes a high-frequency intensity modulator 146 arranged between laser 46 and beam splitter 48. The laser may be the same as that disclosed in the embodiment of FIG. 1A. Modulator 146 may be of any known type, such as acousto-optic, electro-optic or elasto-optic.

Output 148 from modulated light source 144 is split into components 150 and 152. Reference beam component 150 is directed toward a reference photodetector 56 while output beam component 152 passes through planar mirror 56 having a central aperture 58, and is deflected off of a curved mirror 60 to contact and excite a sensor 142 of a selected vial 32.

A modulated emission 154 generated by a particular sensor 142 is time modulated in response to increasing biological activity. It is the modulation rather than intensity that is primarily monitored by detector module 64. As long as the modulation can be measured, a determination of biological activity can be made. Therefore, minor vial mispositioning, light source or detector module aging, and dark current changes such as those resulting from outside light leakage into incubator 44, are not critical.

Currently available fluorescence decay time sensors require high light modulation frequencies, typically above 100 MHz. In known systems with individual light sources at each vial 32, green light emitting diodes ("LED"s) are used. LEDs cannot be modulated at such high frequencies. In apparatus 140, however, with laser 46 and modulator 146, high-frequency intensity modulation may be easily accomplished. Since only a single laser is necessary, the use of a laser which is more expensive then an LED is still practical.

Figure 6:
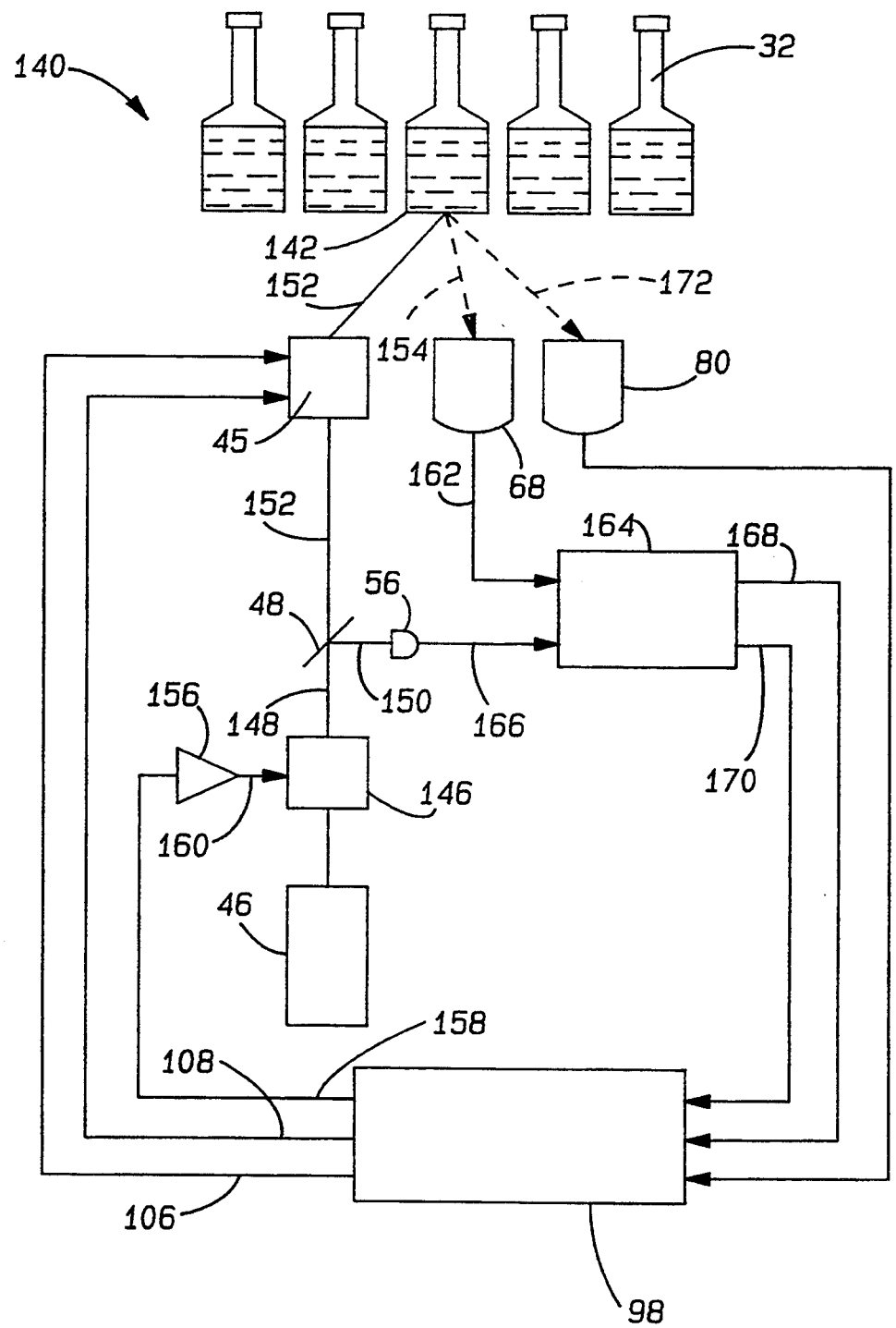
FIG. 6 is a schematic of a control system associated with the system of FIG. 5.

As shown schematically in FIG. 6, controller 98 controls modulator 146 using an amplifier 156. Controller 98 sends a signal 158 to amplifier 156, and an output signal 160 from amplifier 156 is sent to modulator 146. Beam splitter 48 splits output beam 148 from modulator 146 into reference beam component 150 and output beam component 152. With XY translation stage 45 correctly positioned, output beam component 152 is directed to a preselected sensor 142 associated with a vial 32. Sensor 142 selectively generates a modulated sensor emission 154. Photodetector 68 monitors sensor emission 154 and generates a modulated photocurrent 162 which is routed to a vector voltmeter 164. Reference photodetector 56 monitors reference beam component 150 and generates a modulated reference photocurrent 166 which is also routed to vector voltmeter 164. Vector voltmeter 164 compares photocurrents 162 and 166 to determine a sensor phase shift a modulation, and, optionally, sensor intensity. This information is fed into controller 98 via voltmeter outputs 168 and 170 so that a determination may be reached regarding microorganism growth for each vial. As in the embodiment of FIG. 1A, besides storing inputs 168 and 170, computer 98 controls the positioning of XY translation stage 45 using X output channel line 106 and Y output channel line 108. Output beam component 152 is directed serially from sensor to sensor. Thus, a determination of microorganism growth can be made for each vial 32. Backscattered light 172 may also be detected by photodetector 80, as discussed above, to more accurately position XY translation stage 45 and read the bar code information.

Over an extended period of use an XY translation stage may lose some position accuracy. Further, bar code patterns must be accurately positioned. In addition, the vial racks are movable to allow for vial agitation. If the racks are not always stopped at exactly the same position, it may become difficult to read either the sensors or the bar code patterns. Although the positioning steps discussed above address these areas, a microorganism detection system 180 is illustrated in FIG. 7 which is particularly suited to address these areas.

As in the embodiment of FIG. 1A, at least one intensity-based chemical sensor such as a fluorescence sensor 38 is placed on an inner bottom surface 40 of a vial 32 and bar code 82 (see FIG. 2) is placed on a bottom outer surface 84. A plurality of vials 32 are arranged on one or more tipping racks 42 within incubator 44. A plurality of light sources 182 and light sources 184 (which may be LEDs) filters 186, an optical lens 188, and a CCD camera 190 are mounted on a test station 192 of a low-precision XY translation stage 194 within the incubator 44. A CCD camera is a charge coupled device which is an off-the-shelf item. As one example, an acceptable camera is available from Photometrics of Tucson, Ariz. The purpose of the filters 186 is to remove any long wavelength light from the light sources 182 or 184 reading the vial. Although the LEDs are preferably selected to emit in the short wavelength green or blue range, it is inevitable that there will be some red emission. Such red emission could be reflected off of the sensors and back to the CCD camera where they will be interpreted as being part of the emission from the sensor. As such, the filters 186 are incorporated to block such red light from reaching the sensors. A spectral filter 196 is disposed between lens 188 and CCD camera 190. Filter 196 blocks any short wavelength light from the light sources 182 or 184 from reaching the camera matrix 244. In one preferred embodiment, light sources 182 emit light spectrally overlapping with the chemical sensor emission. Thus, the bar code patterns do not have to be composed of a fluorescent dye of the same emission spectrum as the sensor, as discussed above with respect to bar code 82. Light sources 184 emit light in the spectral range necessary to excite the chemical sensors in the presence of biological activity. The use of a plurality of light sources 184 is a low cost alternative to the use of single light source such as a laser.

Figure 7:
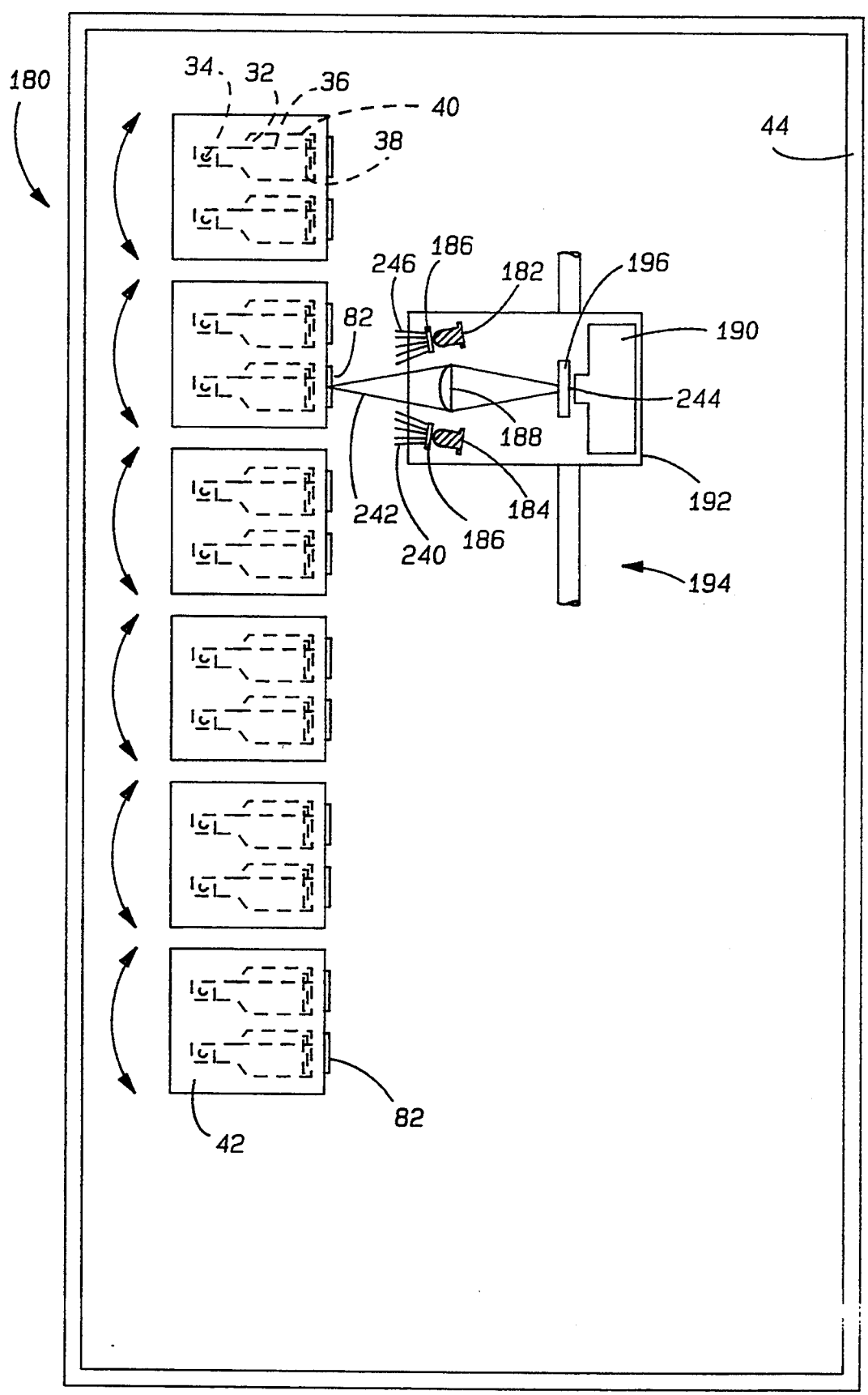
FIG. 7 shows a fourth embodiment of a system according to the present invention.
Figure 8:
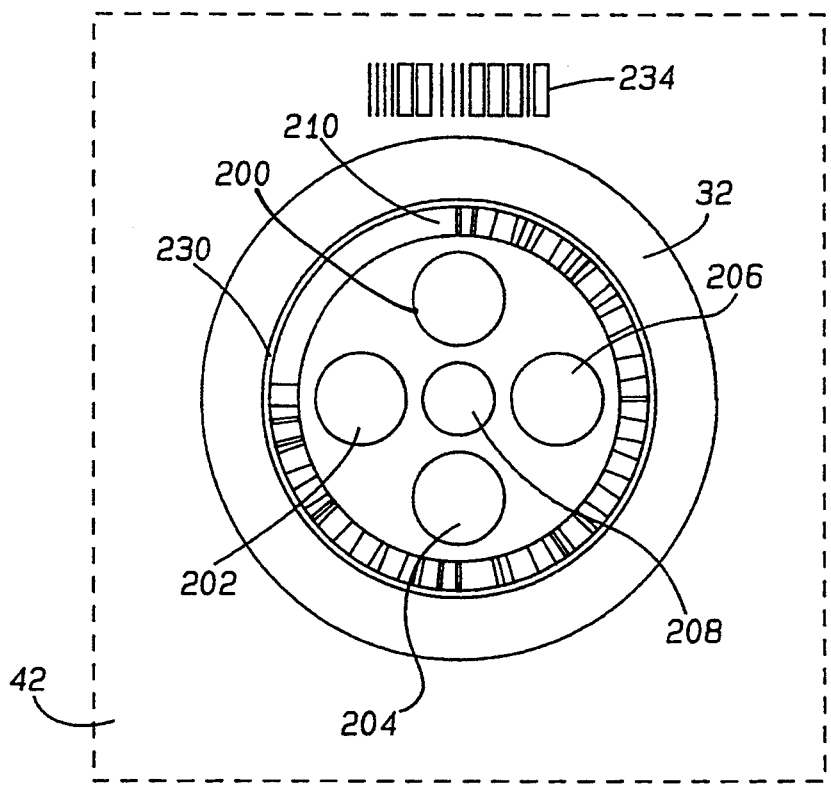
FIG. 8 shows a vial bottom with a plurality of distinct sensors, and a bar code pattern.

As shown in FIG. 8, a plurality of chemical sensors may be used with the present invention, and in particular with the system as shown in FIG. 7. Sensors 200, 202, 204, and 206 each cover small circular areas preferably distributed in a predefined pattern, as discussed further below. Each of these sensors responds to a different chemical parameter such as pH, $CO_2$, $O_2$, or others. Fluorophore 208 is insensitive to chemical inputs, and is utilized as a reference fluorophore for calibration purposes. In this way, changes in excitation light intensity or sensitivity of CCD camera 190 may be detected and cancelled out. A circular bar code pattern 210 is shown in FIG. 8.

The several types of sensors allow plural types of tests to be performed on each vial. To this end, the disclosed test station can be aligned with each sensor, excite that sensor, and read its emission. Positioning steps as described above are used to align the test station with the sensors. The various reference positions facilitate this positioning. The controller records the readings for each type of sensor which is used.

Figure 9:
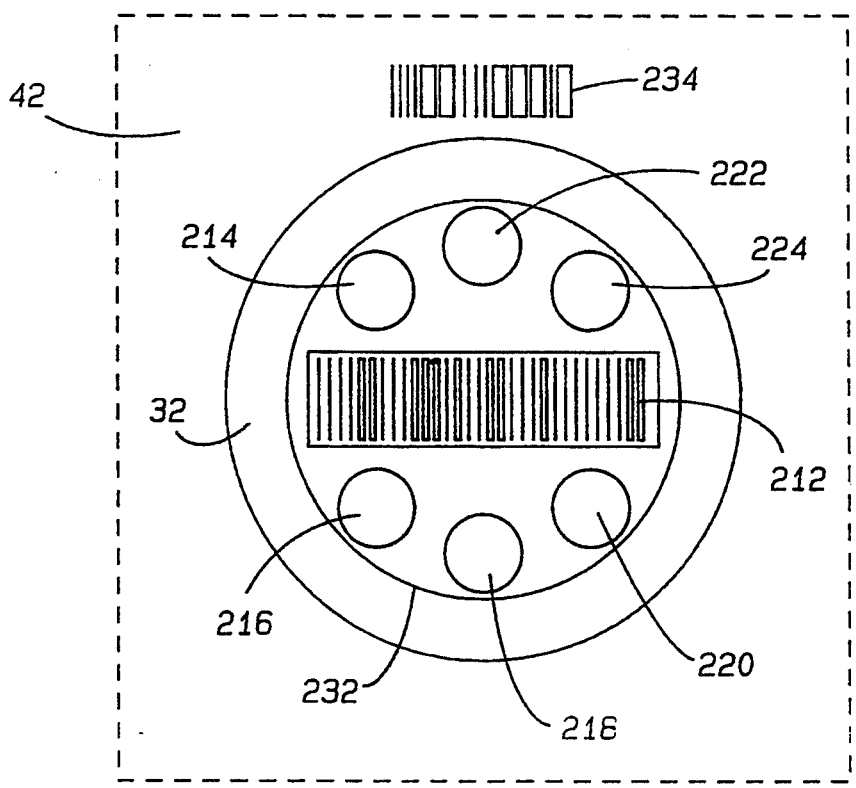
FIG. 9 shows a vial bottom with a plurality of sensors, and a bar code pattern.

A linear bar code pattern 212 such as that illustrated in FIG. 9 may also be used. Once again, a plurality of sensors 214, 216, 218, 220, and 222 distributed in a predefined pattern are used with a reference fluorophore 224 used for calibration. Preferably the bar codes and sensors of FIGS. 8 and 9 are printed on a label such that they are properly positioned relative to each other.

The positions of patterns 210 and 212 may be used to check and to control the position of test station 192. Both bar code patterns 210 and 212 preferably also have a well-defined spatial correlation with the illustrated predefined pattern of chemical sensor distribution. In the case of linear bar code pattern 212, for example, its angular orientation may be used to provide reference position information with regard to the individual chemical sensors on the bottom inner surface 40 of the vial. The circular bar code pattern is shown limited to approximately 270 degrees with the gap used for a similar reference position function.

FIGS. 8 and 9 also illustrate the use of concentric circles 230 and 232, respectively. As discussed above with respect to bar code 82, concentric circles 230 and 232 may be used as position encoders. Even if a particular label is attached slightly eccentrically to the bottom surface 84 of a vial 32, no bar code reading errors occurs, since the circle and the bar code pattern are printed concentrically with respect to each other.

Finally, FIGS. 8 and 9 also illustrate the use of a bar code pattern 234 placed on a bottom surface of the tipping rack 42, shown schematically, adjacent each vial. Pattern 234 includes vial station number information and may be used to check the position of the test station.

In operation, system 180 of FIG. 7 includes a system controller 98 such as a computer (not shown) that directs test station 192 from its home position to a preselected first vial 32. After test station 192 has arrived at the first vial 32, the computer turns on the illumination light sources 184, generating output beams 240. A reflection 242 from vial 32 is imaged onto a matrix 244 of the CCD camera 190 by lens 188. Spectral emission filter 196 prevents scattered light from output beams 240 from reaching the CCD matrix 244. The image received by camera 190 is stored in the controller's memory and analyzed for the position of the concentric circles 230 or 232 and/or the bar code pattern relative to the center of the CCD matrix 244. The controller calculates the necessary X and Y corrections for the test station 192 to move the circles into a desired or central position on the CCD matrix 244. After the test station 192 is moved to a new position, the first stored image is deleted and a new one is recorded, stored, and analyzed. This procedure is repeated until a given positioning tolerance is achieved. By monitoring the relative position of the camera 190 and the circles 230 or 232, and adjusting the position of test station 192 one ensures the test station is properly positioned relative to the bar code pattern. Then, the last recorded image is used to perform a software bar code reading of the label attached to the bottom 84 of a vial 32. At this point, bar code pattern 234 may be read for information concerning the vial station number. A similar positioning logic is used with the earlier disclosed embodiments. This allows a confirmation of the correct position of the test station 192 relative to the vial station number. This may be of particular importance after a system interrupt has occurred. The two bar code readings can be performed very quickly because the corresponding patterns are always in the same position. After the bar codes have been read, the image is deleted.

Once the bar code information is recorded, the controller activates light sources 182 to generate output beams 246. Reflection 242, including selected emissions from the sensors and reference fluorophore is imaged by lens 188 and detected by the CCD camera 190. Once again, filter 196 prevents scattered light from light sources 182 from reaching the CCD matrix 244. The image, including the intensity of the selected sensors are analyzed and stored. The test station 192 is then moved to the next vial 32. Because test station 192 moves from a well-defined position with respect to each vial, any accumulation of position error is unlikely.

Figure 10:
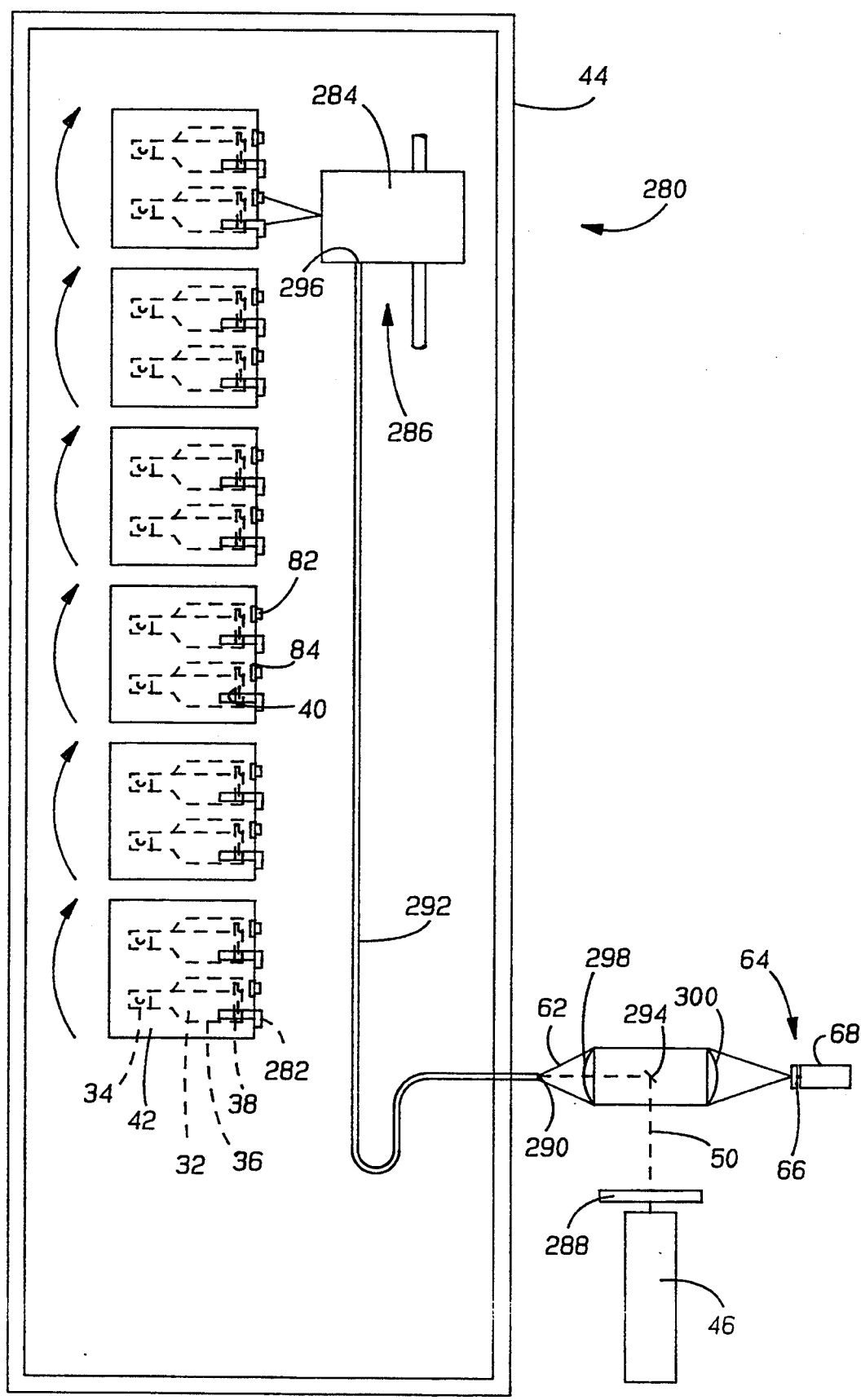
FIG. 10 shows a fifth embodiment of a system according to the present invention.

FIG. 10 illustrates an embodiment of the present invention utilizing more than one detection method. System 280 comprises vials 32 sealed with a septurn 34 and containing a medium/blood mixture 36. Vials 32 contain a fluorescent chemical sensor 38 disposed on an inner bottom surface 40 of each of vials 32, and a bar code label 82 on the outer vial bottom 84. Racks 42 include two plastic light guide stubs 282 at each vial station.

Read-out of the bar code pattern 88 on label 82 as well as utilization of fluorescence detection and scattered photon migration ("SPM") at each vial 32 are accomplished by moving the test station 284 of an XY translation stage 286 to each vial station. A light source 46, such as that discussed with respect to the embodiment of FIG. 1A, is mounted outside of incubator 44. An output beam 50 passes through a spectral filter 288, and is then directed into an input end 290 of a fiber-optic bundle 292 by a mirror 294. Filter 288 removes any red light from the light source 46 which could back scatter towards the detector. An output end 296 of fiber-optic bundle 292 is mounted onto test station 284, shown schematically in FIG. 10. A fluorescence emission 62 from a sensor 38 of a select vial 32 is directed into output end 296, reemerges from input end 290, and is focused onto a detector module 64 using a pair of lenses 298 and 300. As discussed above with respect to the embodiment of FIG. 1A, detector module 64 comprises a high-sensitivity photodetector 68 and a spectral emission filter 66, arranged at the input of photodetector 68 to remove backscattered light from light source 46.

Figure 11:
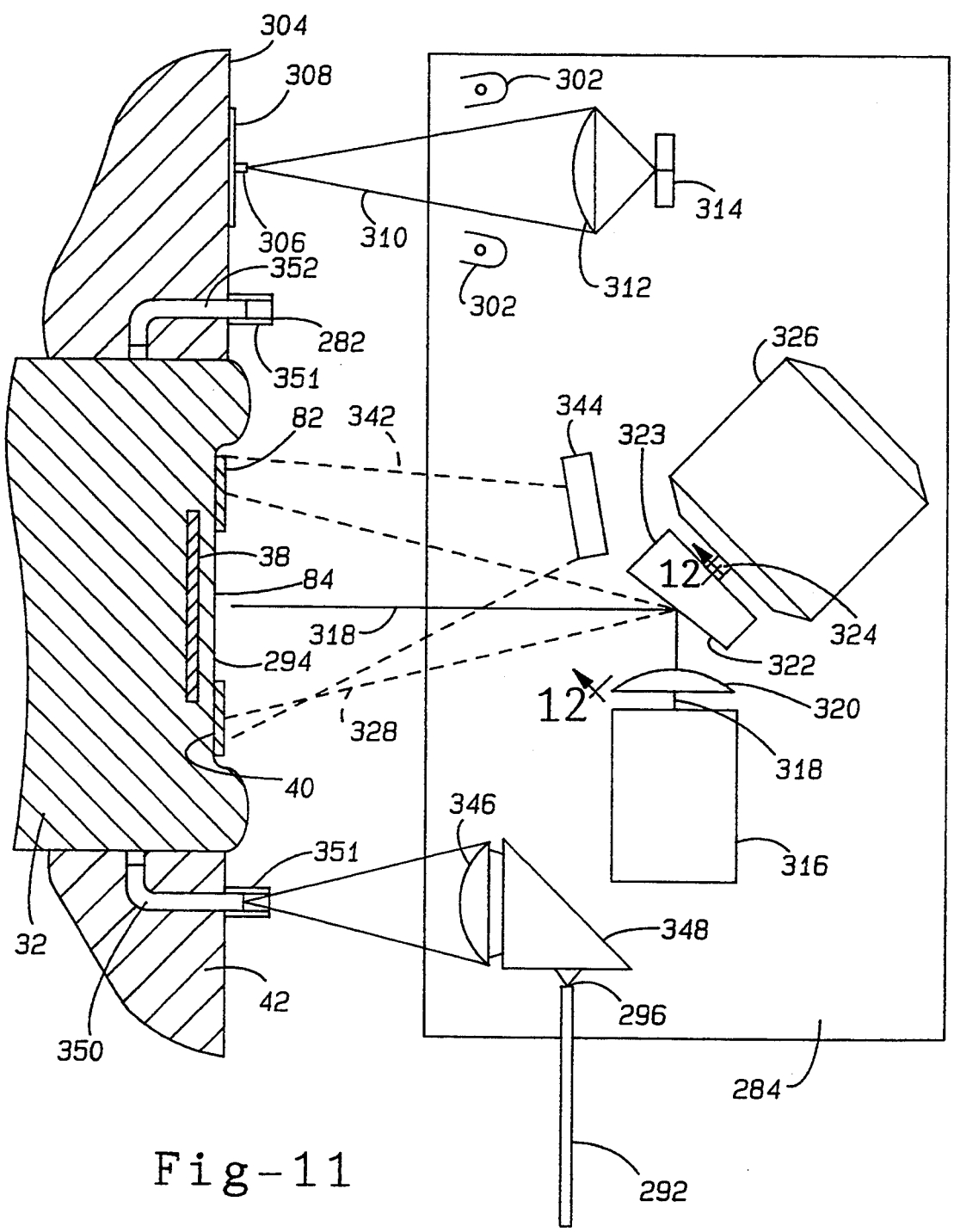
FIG. 11 depicts details of the rack area close to a vial bottom for the embodiment of FIG. 10.

FIG. 11 depicts details of the rack area close to the bottoms of vials 32, and shows the elements which are mounted on the test station 284. The inner bottom 40 of each vial 32 is covered with a fluorescent chemical sensor 38. The outer bottom 84 of each vial is covered with a circular bar code label 82 that leaves a central bottom area 294 open to expose sensor 38. Test station 284 is arranged parallel to all vial bottoms whenever a bar code reading or a sensor reading is performed.

In operation, test station 284 is directed from its home position to a first vial 32. After test station 284 has arrived at a first vial station, the system controller turns on one or more illumination sources 302 mounted on the test station 284 such that a preselected portion 304 of a bottom surface of a rack 42 is illuminated. Bottom surface portion 304 includes a carefully positioned highly backscattering spot 306 surrounded by a weak backscattering area 308. The backscattered light 310 is imaged by a first lens 312 onto a four-quadrant photodiode 314. Depending on the current position of the test station, the four-quadrant photodiode 314 will create two error signals that contain information regarding the deviation of the test station 284 from the correct position in both the X and Y directions. These two error signals are fed to the system controller which then directs the test station 284 towards the correct position. In a sense the test station is moved to center the light on spot 306. The error signals of the four-quadrant photodiode 314 become equal to zero if the correct position is reached.

Once the correct position is reached, the system controller turns off illumination light sources 302 and activates a diode laser 316. An output beam 318 from laser 316 is focused by a second lens 320 and directed towards the vial bottom by means of a mirror 322. Mirror 322 is mounted on a cylinder 323 which, in turn, is mounted onto a shaft 324 of a small electrical motor 326. The diode laser 316 and mirror 322 are arranged on the test station 284 in such a position that the output beam 318 impinges exactly at the center of the circular bar code pattern of label 82 after the position correction has been accomplished by means of the four-quadrant photodiode 314.

The system controller 98 then turns on the electric motor 326 to rotate shaft 324, which carries mirror 322. During rotation of shaft 324, the mirror 322 is tilted off by a certain angle from a preferred 90 degree orientation relative to the motor axis 324. During this tilting, a deflected beam 328 is moved along the circumference of a circle on the vial bottom 84 containing the bar code pattern 88. This embodiment allows for fast bar code reading.

Figure 12:
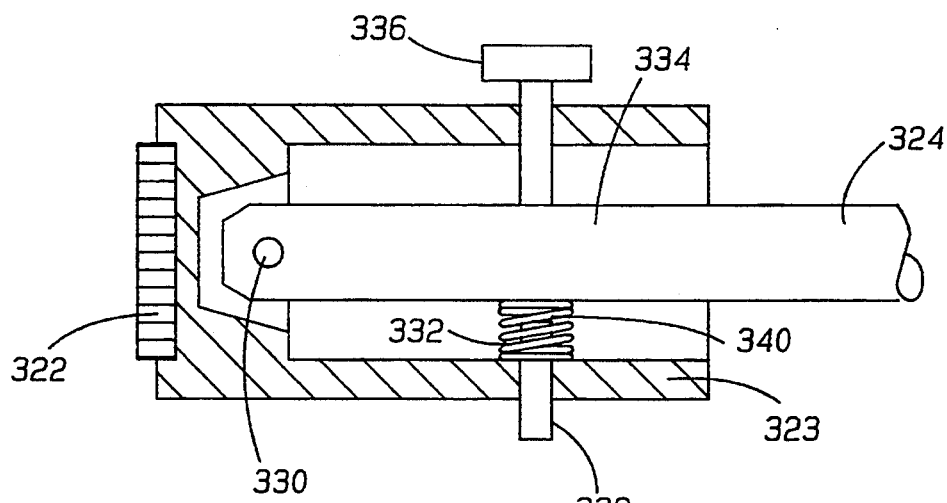
FIG. 12 is a cross-sectional view taken along line 12—12 of FIG. 11.

FIG. 12 depicts one possible way of tilting mirror 322 during rotation of the motor shaft 324. The cylinder 323 is mounted to shaft 324 via a pivot pin link 330. If the shaft 324 is at rest, a spring 332 forces cylinder 323 into a position where an outer surface 334 of a screw 336 touches shaft 324. By adjusting screw 336, an exact 90 degree orientation of mirror 322 with respect to the axis of shaft 324 is established.

To read out bar code pattern 88 after the correct position has been determined, motor 326 is started with resulting rotation of cylinder 323. Screw 336 is designed so that its mass is larger than the mass of a second screw 338 arranged at an opposite position with regard to screw 336 on cylinder 323. Due to the mass difference between screws 336 and 338, centrifugal force causes the cylinder 323 to tilt around link 330. The tilting will continue until an end 340 of screw 338 touches shaft 324. By adjusting screw 338 accordingly, the maximum tilting angle may be tuned to an optimal value. Once this final tilting angle is achieved the deflected beam 328 will correctly scan the bar code pattern. Once this pattern is read, the motor 326 is stopped and the cylinder 323 with mirror 322 are returned to the home-position, i.e., to a 90 degree orientation relative to the shaft axis.

As shown in FIG. 11, the light 342 backscattered from the bar code pattern is monitored by a photodetector 344 mounted on the test station 284 close to the diode laser 316. The bar code information is stored and analyzed in the system controller.

It is also possible to print an additional 3-digit bar code pattern onto the vial rack 42 close to each vial station. As discussed above with respect to FIGS. 8 and 9, this allows for address checking. To read this bar code, the system controller directs the test station to the corresponding area and moves the test station 284 so that the diode laser beam 318 scans the bar code.

After the appropriate bar code patterns have been read, the system controller turns off the diode laser 316 and directs the test station 284 to a position where a third lens 346 on the test station 284 is positioned opposite the center of the vial bottom. This position is not illustrated in FIG. 11, but would include the test station 284 being moved vertically upwardly from the illustrated position. The system controller then turns on the light source 46, see FIG. 10, outside of incubator 44. As mentioned above, the output beam 50 passes a spectral filter 288, and is then directed into the input end 290 of bundle 292 by mirror 294. Output beam 50 reemerging from the output end 296 is deflected by a prism 348 towards the center of the inner vial bottom 40 that is covered with the fluorescent chemical sensor 38. The resulting emission by sensor 38 is focused by the same third lens 346 into the output end 296. The fluorescence light reemerging from the input end 290 of the bundle 292 is focused by lenses 298 and 300, as discussed above, onto detector module 64. The output signal of the high-sensitivity photodetector 68 is fed to the system controller where it is stored and analyzed.

As shown in FIG. 11, two plastic light guide stubs 350 are arranged close to each vial 32 on the rack 42 to perform an SPM measurement. Tube covers 351 center light into and out of stubs 350. In practice (not shown to correct scale in FIG. 11) the distance between the diode laser beam 318 and the third lens 346 is selected to match the distance between the two plastic light guide stubs 350. This allows the test station 284 to be directed to a position where the output beam 318 is directed into one of the stubs 350, and light reemerging from the other stub is directed into the third lens 346, the prism 348, the bundle 292, and the high-sensitivity photodetector 68 for SPM detection. Preferably, the wavelength of the diode laser 316 falls within the spectral range of the fluorescence emission from the chemical sensor. Essentially, the SPM testing procedure involves directing a light into a vial and then monitoring the reemerging light. By monitoring the reemerging light a determination can be made of whether bacterial activity is occurring in the vial.

Finally, after storing and analyzing the SPM and fluorescence signals, the system controller directs the test station 284 of the XY translation stage to the next vial station. As mentioned previously, because the test station starts to move from a well-defined position, any accumulation of positioning errors is unlikely.

Figure 13:
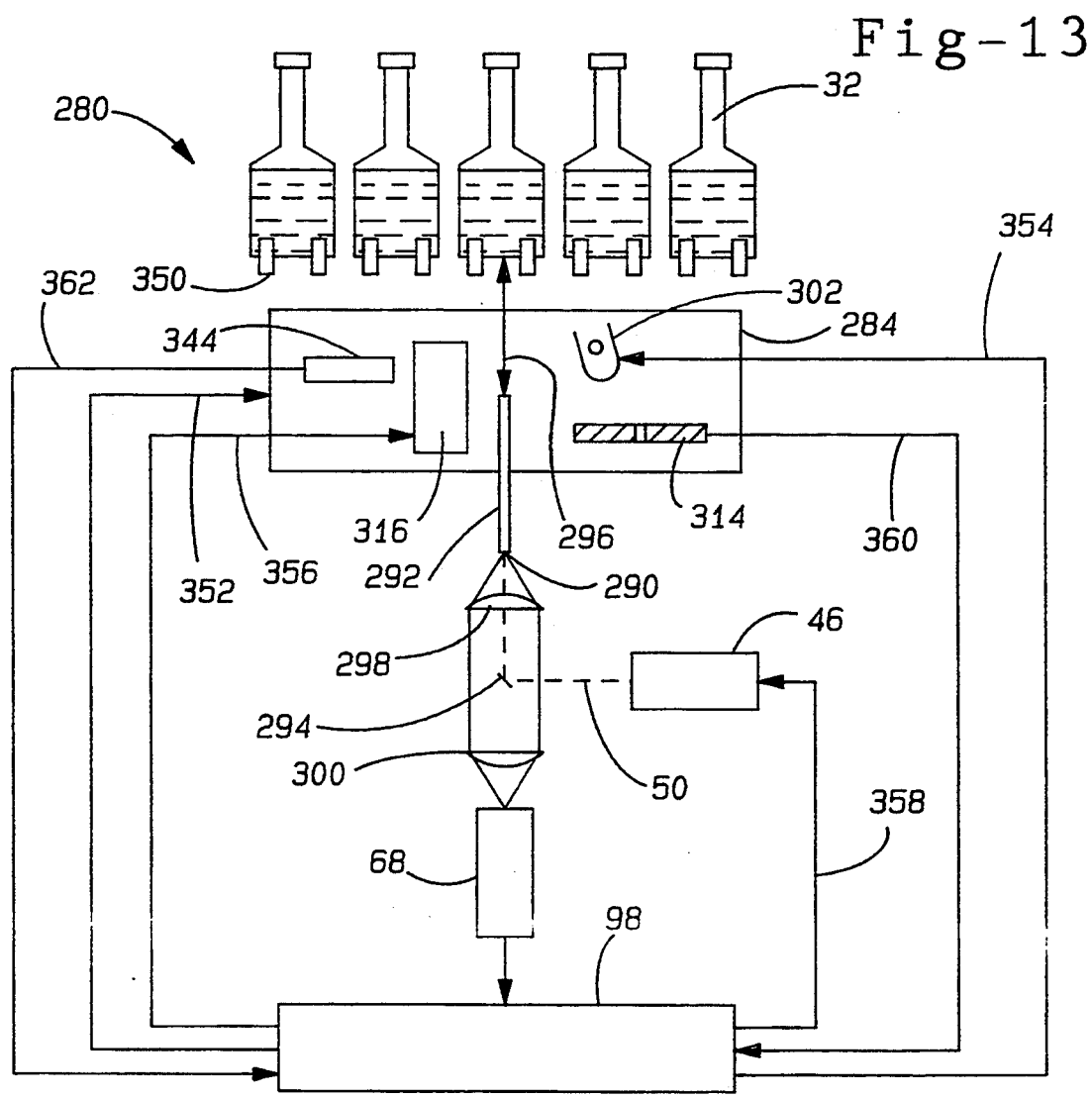
FIG. 13 is a schematic illustrating the main optical and electronic components of the embodiment of FIG. 10.

FIG. 13 is a schematic illustrating the main optical and electronic components of system 280. The system controller 98 controls the positioning of test station 284 via line 352, illumination of light sources 302 via line 354, diode laser 316 via line 356, and light source 46 via line 358, as discussed above. The output signals 360, 362, and 364 from four-quadrant photodiode 314, bar code reading photodetector 344, and from high-sensitivity photodetector 68, respectively, are all fed to system controller 98 where they are stored and analyzed.

Figure 14:
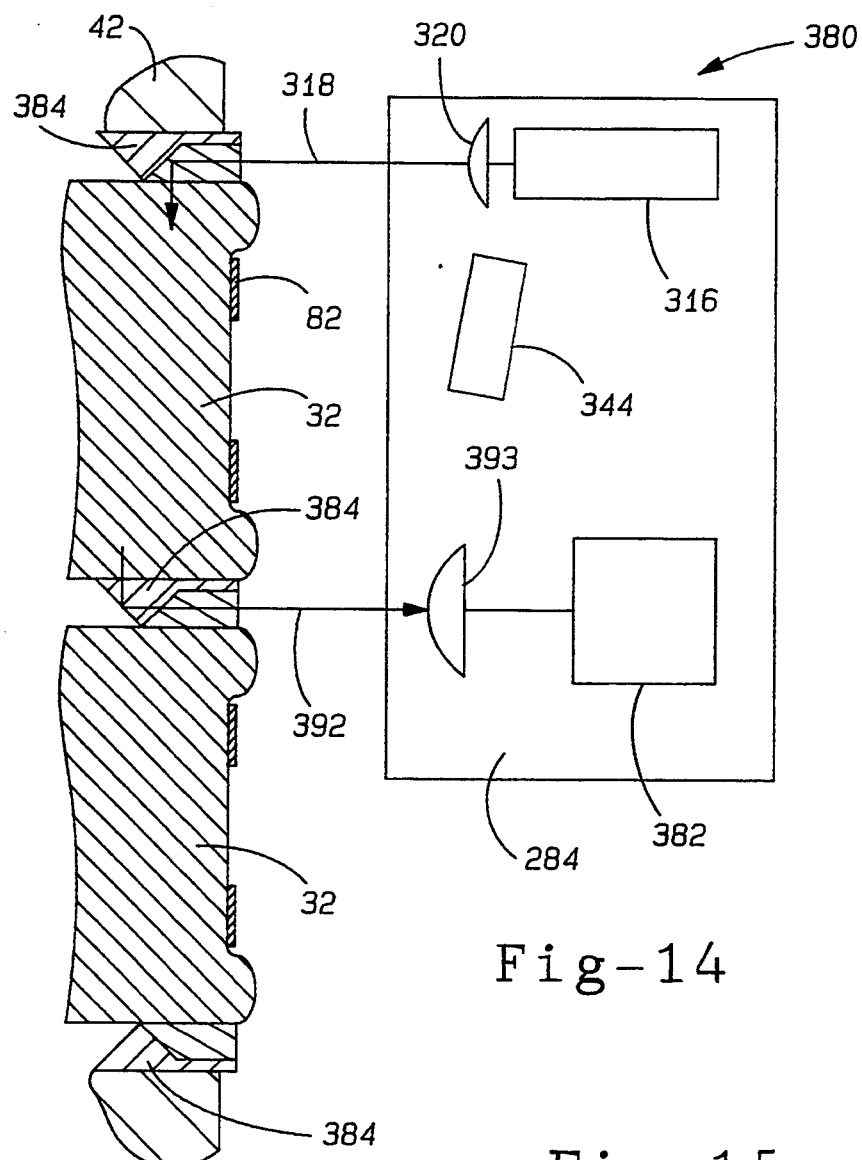
FIG. 14 shows a sixth embodiment of a system according to the present invention.

A simplified SPM photodetector 380 having a laser 316, lens 320 and laser beam 318 is illustrated in FIG. 14. Rather than using a fiber optic bundle, an SPM photodetector 382 is shown on test station 284. The distance between the laser beam 318 and photodetector 382 are equal to the distance between two adjacent light stubs 384 on opposite sides of a vial 32.

Figure 15:
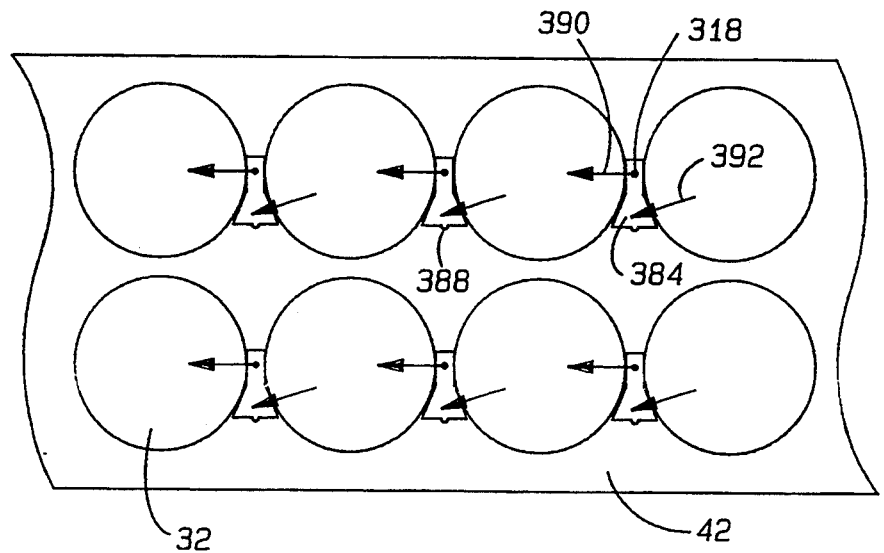
FIG. 15 is a planar view of a portion of the embodiment of FIG. 14.

As shown in FIG. 15, light stubs 384 are placed between adjacent vial openings of a vial rack 42. A stub 384 is held in position by a small key 388. Stub 384 provides two functions. First, the stub deflects the SPM excitation beam 318 into a second beam 390 that is directed towards a left vial. Second, the stub 384 deflects light 392 reemerging from the right vial towards the SPM photodetector 382.

Figure 16:
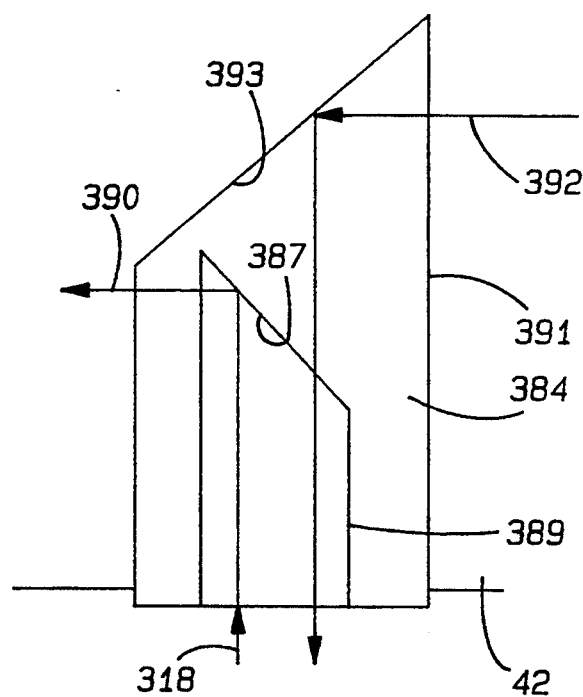
FIG. 16 is a cross-section of a light guide stub of the embodiment of FIG. 14.

The structure of the light guide 384 is shown in greater detail in FIG. 16. This light guide embodiment has the advantage that only one light stub is needed per vial 32. As shown, stub 384 includes a larger portion 391 which receives the light 392, deflects that light off an inclined face 393, and passes that light outwardly of the guide stub 384 as described. Further, a smaller portion 389 has an inclined face 387 which deflects the light 318 into a vial as described at 390. The stubs are preferably formed on an acrylic, polymethyl methacrylate is preferred.

Figure 17:
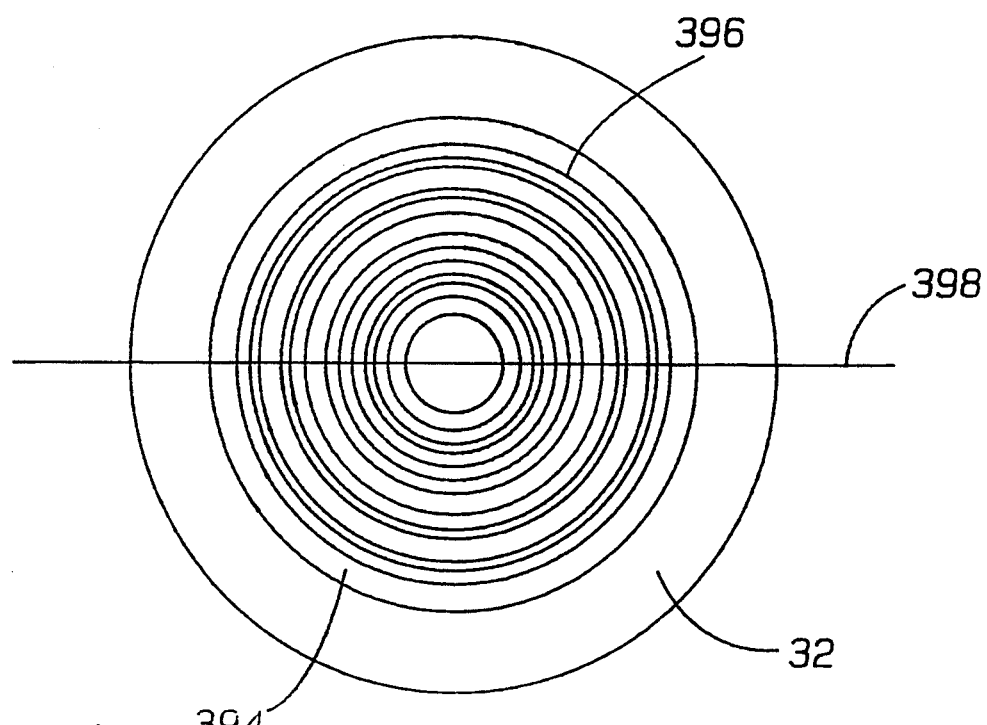
FIG. 17 shows a vial bottom with a bar code pattern.

When using system 380 according to the present invention, bar code reading at each vial may be accomplished in a unique way. As illustrated in FIG. 17, a bar code pattern 394 is printed as a system of concentric circles 396. As the SPM excitation beam is directed from one vial to the next, it crosses the bar code pattern 394 on a diameter 398. During this crossing the system can read out the bar code pattern.

This application makes reference to light being used to excite the sensor. It should be understood that any type of radiation could fall within the scope of this language.

Preferred embodiments of the present invention have been described. It is to be understood that variations and modifications may be employed without departing from the scope of the present invention. Accordingly, the following claims should be studied to learn the true scope of the present invention.

I claim:

1. A method for monitoring bacterial growth in a plurality of sample vials comprising the steps of:
   (1) disposing a plurality of sample vials in a bacterial growth detection system;
   (2) positioning a bacterial growth detection station on a moving frame mounted in said bacterial growth detection system, said bacterial growth detection station being capable of gathering information for making a determination of whether each of said vials is experiencing bacterial growth;
   (3) moving said bacterial growth detection station adjacent to each of said vials, and making a determination of whether the particular vial is experiencing bacterial growth;
   (4) providing said bacterial growth detection station with the capability of gathering a first and second type of information for making a determination of whether each of said vials is experiencing bacterial growth, wherein said second type of information is provided by a sensor in each of said vials; and
   (5) providing said bacterial growth detection station with a first light radiation source at a first location, a detector at a second location spaced from said first location by a first distance, and a pair of light stubs spaced by a distance which approximates said first distance and positioned adjacent to each of said vials, and directing said first light radiation into one of said stubs, and the other of said stubs directing a reflected radiation out of a sample vial and into said detector to provide said first type of information with regard to whether the sample vial is experiencing bacterial growth.

2. A method as recited in claim 1, wherein said plurality of sample vials are positioned in a two dimensional array, and said bacterial growth detection station is moved along two dimensions such that said bacterial growth detection station periodically makes a determination of whether each of said vials is experiencing bacterial growth.

3. A method as recited in claim 1, wherein said moving frame is positioned at a proper location relative to a vial to be tested by directing a beam of electromagnetic radiation from said moving frame to a reference location associated with said vial, and monitoring the location of said reference location, and further correcting the position of said moving frame such that said moving frame is properly positioned relative to said reference location.

4. A method as recited in claim 3, wherein said reference location used to position said moving frame is associated with a bar code label mounted on said vial.

5. A method as recited in claim 3, wherein said reference location used to position said moving frame is associated with a plurality of distinct types of sensors located on an inner bottom surface of said vial.

6. A method as recited in claim 5, wherein several of said distinct types of sensors located on said inner bottom surface of said vial are used to make the determination of bacterial growth by gathering said second type of information.

7. A method as recited in claim 1, wherein a bar code label containing information is attached to each of said vials.

8. A method as recited in claim 1 wherein the determination of bacterial growth by gathering said second type of information is accomplished by moving said bacterial growth detection station in a circle around a bottom surface of each sample vial.

9. A method as recited in claim 8, wherein a bar code label containing information is printed on a bottom surface of each sample vial, and said bacterial growth detection station carries an apparatus for reading said bar code information, said bacterial growth detection station being moved in a circle around said bottom surface of each sample vial to read said bar code label containing information, and also being moved in a circle around said bottom surface to make a determination of whether each sample vial is experiencing bacterial growth by gathering said second type of information.

10. A method of identifying and monitoring bacterial growth in a sample vial comprising the steps of:
(1) placing a bar code on each of a plurality of sample vials, said bar code containing information with regard to each of said sample vial;
(2) mounting said plurality of sample vials within a bacterial growth detection system;
(3) positioning a detection station in said bacterial growth detection system to read said bar code from each sample vial and detect whether each sample vial is experiencing bacterial growth, wherein said detection station is mounted on a moving frame which is moved serially along said plurality of sample vials;
(4) providing said detection station with the capability of gathering a first and second type of information for making a determination of whether each of said vials is experiencing bacterial growth, wherein said second type of information is provided by a sensor in each of said vials; and
(5) providing said detection station with a first light radiation source at a first location, a detector at a second location spaced from said first location by a first distance, and a pair of light stubs spaced by a distance which approximates said first distance and positioned adjacent to each of said vials, and directing said first light radiation into one of said stubs, and the other of said stubs directing a reflected radiation out of a sample vial and into said detector to provide said first type of information with regard to whether the sample vial is experiencing bacterial growth.

11. A method as recited in claim 10, wherein said bar code is printed with a reference indicia, and said reference indicia is used to properly position said detection station relative to said bar code prior to reading said bar code.

12. A method as recited in claim 10, wherein said bar code is also printed in a known location on each of said vials relative to a plurality of distinct types of sensors located on an inner bottom surface of each of said vials, and the location of said bar code is used to provide an indication of the positions of said sensors such that one is able to make a determination of whether said sensors are identifying bacterial growth within each sample vial.

13. A method as recited in claim 10, wherein said bar code is provided by a plurality of concentric circles located on a bottom surface of each of said sample vials, each bar code containing information with regard to a corresponding sample vial, wherein said detection station scans across said concentric circles to read said bar code.

* * * * *